United States Patent [19]

Babb et al.

[11] Patent Number: 5,364,547

[45] Date of Patent: * Nov. 15, 1994

[54] LUBRICANTS CONTAINING PERFLUOROCYCLOBUTANE RINGS

[75] Inventors: David A. Babb, Lake Jackson, Tex.; Ted A. Morgan, Midland, Mich.

[73] Assignee: The Dow Chemical Company, Midland, Mich.

[*] Notice: The portion of the term of this patent subsequent to Apr. 26, 2010 has been disclaimed.

[21] Appl. No.: 54,647

[22] Filed: Apr. 26, 1993

Related U.S. Application Data

[60] Continuation-in-part of Ser. No. 929,742, Aug. 13, 1992, abandoned, which is a division of Ser. No. 673,882, Mar. 22, 1991, Pat. No. 5,159,038, which is a division of Ser. No. 364,667, Jun. 9, 1989, Pat. No. 5,037,917, and Ser. No. 625,588, Dec. 10, 1990, Pat. No. 5,246,782.

[51] Int. Cl.$^5$ ............... C10M 105/50; C10M 105/18
[52] U.S. Cl. ................................... 252/54; 526/242; 526/243; 526/244; 526/255
[58] Field of Search .................. 252/54; 526/242, 243, 526/244, 255

[56] References Cited

U.S. PATENT DOCUMENTS

| | | |
|---|---|---|
| Re. 23,425 | 10/1951 | Harmon . |
| 2,848,504 | 8/1958 | Dixon . |
| 2,958,685 | 11/1960 | Eleuterio . |
| 2,982,786 | 5/1961 | McCane . |
| 3,022,356 | 2/1962 | Nooy . |
| 3,111,509 | 11/1963 | Folt . |
| 3,114,778 | 12/1963 | Fritz et al. . |
| 3,277,068 | 10/1966 | Wall et al. . |
| 3,303,145 | 2/1967 | Carlson . |
| 3,310,606 | 3/1967 | Fritz . |
| 3,316,312 | 4/1967 | McCane et al. . |
| 3,505,411 | 4/1970 | Rice . |
| 3,549,606 | 12/1970 | Gash . |
| 3,696,154 | 10/1972 | Anderson . |
| 3,840,603 | 10/1974 | Anderson et al. . |
| 3,900,380 | 8/1975 | Anderson et al. . |
| 4,154,753 | 5/1979 | Fielding . |
| 4,377,711 | 3/1983 | Rico et al. . |
| 4,423,249 | 12/1983 | Carl et al. . |
| 5,021,602 | 6/1991 | Clement et al. . |
| 5,023,380 | 6/1991 | Babb et al. . |
| 5,037,917 | 8/1991 | Babb et al. . |
| 5,037,918 | 8/1991 | Babb . |
| 5,037,919 | 8/1991 | Clement et al. . |
| 5,066,746 | 11/1991 | Clement et al. . |
| 5,159,036 | 10/1992 | Babb . |
| 5,162,468 | 11/1992 | Babb et al. . |
| 5,198,513 | 3/1993 | Clement et al. . |
| 5,210,265 | 5/1993 | Clement et al. . |
| 5,246,782 | 9/1993 | Kennedy et al. ................ 428/421 |

FOREIGN PATENT DOCUMENTS

| | | |
|---|---|---|
| 030292 | 2/1989 | European Pat. Off. . |
| 0490335 | 6/1992 | European Pat. Off. . |
| 1481730 | 4/1967 | France . |
| 3024018 | 1/1981 | Germany . |
| 1126554 | 10/1968 | United Kingdom . |
| 1185564 | 3/1970 | United Kingdom . |
| 90/15042 | 12/1990 | WIPO . |
| 90/15043 | 12/1990 | WIPO . |
| 90/15044 | 12/1990 | WIPO . |
| 90/15082 | 12/1990 | WIPO . |

OTHER PUBLICATIONS

Chem. Abstract-59:8879c date unavailable.
Chem. Abstract-77:34091k date unavailable.
Chem. Abstract-105:171569h, date unavailable.
Coffman et al. "Synthesis of Tetrafluorocyclobutanes by Cycloalkylation" in *J. Chem. Soc.* vol. 71 (1949), pp. 490–496.

(List continued on next page.)

*Primary Examiner*—Jaqueline V. Howard

[57] ABSTRACT

A new lubricant comprises at least one compound having a perfluorocyclobutane group, preferably a perfluorovinyl aryl ether. The lubricant is conveniently applied from solvents which are not chlorofluorocarbons and is effective at high temperatures e.g., in engines and for magnetic media, either internally or topically.

39 Claims, No Drawings

OTHER PUBLICATIONS

Henne et al. "Contrast in the Dimeriztion of Polychloro-and Polyfluoro-ethylene" in *J Amer Chem. Soc.*, Feb. 1947, pp. 279–281.

Prober "The Synthesis and Polymerization of Some Fluorinated Styrenes" in *J. Amer. Chem. Soc.*, 75, pp. 968–973 (1953) month unknown.

Hauptschein et al. "Thermal Syntheses of Telomers of Fluorinated Olefins. I. Perfluoropropene 1" in *J. Amer. Chem. Soc.*, pp. 2549–2553 (1957) month unknown.

Miller et al., "Cesium Fluoride Catalyzed Rearrangement of Perfluorodienes to Perfluorodialkylacetylenes" in J. Amer. Chem. Soc., (1961) pp. 1767–1768 month unknown.

Brown et al. "Radiation-Induced Polymerization and Other reactions of n-Perfluoropentadiene-1,4 at High Temperature and Pressure" in J. Poly. Sci. Part A-1., vol. 3, (1965), pp. 1641–1660 month unknown.

Fearn et al. "Polymers and Telomers of Perfluoro-1,-4-pentadiene" in J. Poly. Sci. Part A-1., vol. 34, (1966), pp. 131–140 month unknown.

Banks et al. "Polyhalogenoallenes, Part IV. Thermal Co-dimerisation of Tetra-fluoroallene with Hexafluorobut-2-yne" in *J. Chem. Soc.* (1965) pp. 2051–2052 (month unknown).

Sharkey, "The Cycloaddition Reaction of Fluoroolefins" in *Fluorine Chem. Rev.* (1968) pp. 1–53 (month unknown).

Hodgdon et al, "Preparation and Polymerizability of Substituted a,B,B,-Trifluorostyrenes" in *J. Poly. Sci.*, vol. 6 (1968) pp. 711–717 (month unknown).

Chambers, *Fluorine in Organic Chemistry*, John Wiley, New York, (1973), pp. 173–188 (month unknown).

Rico et al., "Condensation of 1,2-Dibromotetrafluoroethane with Various Potassium Thiophenoxides and Phenoxides" in J. Fluorine Chem., (1982), pp. 759–764 (month unknown).

Heinze et al., "Palladium-Catalyzed Cross-Coupling of Perfluoroalkenylzinc Reagents with Aryl Iodiees. A New, Simple Synthesis of a,B,-Trifluorostyrenes and the Stereoselective Preparation of 1-Arylperfluoropropenes" *J. Org. Chem.* (1988) pp. 2714–2720 (month unknown).

Paleta et al. "Haloacrylic Acids. VI. *Ethylene Glycol Bis(Trifluoroacrylate) in Sb.Vsy.SkChem."–Technol., (1976), pp. 5–11 (month unknown).

Glazkov et al. "Cycloaddition of Perfluorovinyl Ethers to Dienes," Bulletin of the Academy of Scien. USSR, (1988) pp. 2137–3141.

Tarrant et al., "The Preparation and Reactions of Some Silanes Containing the Trifluorovinyl Group" in *J. Org. Chem.* vol. 31, No. 4, Apr. 1966, pp. 1143–1146.

LUBRICANTS CONTAINING PERFLUOROCYCLOBUTANE RINGS

BACKGROUND OF THE INVENTION

This application is a continuation-in-pad of U.S. patent application Ser. No. 07/929,742 filed Aug. 13, 1992 now abandoned, which is a divisional application of U.S. patent application Ser. No. 07/673,882 filed Mar. 22, 1991, now U.S. Pat. No. 5,159,038 which is a divisional application of U.S. patent application Ser. No. 07/364,667 filed Jun. 9, 1989; now U.S. Pat. No. 5,037,917 and of U.S. patent application Ser. No. 07/625,588 filed Dec. 10, 1990; now U.S. Pat. No. 5,246,782, all of which are incorporated by reference herein in their entireties.

The present invention is related to lubricants, more particularly lubricants useful over a large temperature range.

Demands placed on existing lubricants are currently undergoing significant changes. Engines are being developed for automotive and aeronautic applications that have requirements dramatically different from those of engines currently in use. It is anticipated that these engines will operate at temperatures exceeding 250° C. and will be constructed using materials new or different from those currently in use. Thus, lubricants or lubricant additives that are stable at the high use temperatures while possessing the other properties required of lubricants will be needed for these applications..

Additionally, lubricants are needed for magnetic recording media such as high density rigid disks, ultra high density floppy disks, digital audio tapes and video tapes which can be read by a magnetic recording head. In use of these media, a recording head is in very close proximity to the recording media and frequently contacts the recording media. Such contact causes wear of the thin layer of magnetic material on the recording media and shortens the useful life of the recording media. With insufficiently effective lubricants there are problems including increased friction, scratching and adhesion. More efficient internal and boundary lubricant systems would be desirable.

Lubricants for magnetic media are known in the art, but such lubricants are generally designed for more mature counter-panns of the magnetic media such as standard audio, VHS video and standard floppy disks. Examples of such lubricants included are described in U.S. Pat. No. 4,613,548 to Lum, issued on Sep. 23, 1986, a normally liquid, low molecular weight linear or cyclic polyfluoroalkoxy phosphazene mixtures. Such lubricants do not demonstrate solvent compatibility with a wide range of organic solvents and are not stable in water and base. A family of perfluoropolyether difunctional derivatives end capped with planar groups including certain carboxylic acids and esters, perfluoroalkyl ethers, hydroxyalkyl, and certain substituted phenyl groups are commercially available from Ausimont U.S.A., Inc., under the trade designation FOMBLIN TM. Certain lubricants having cyclic phosphazenes substituted with fluorinated phenoxy moleties and perfluoroalkylphenoxy moleties are disclosed in U.S. Pat. No. 5,015,405. Such lubricants are not stable at high temperatures (e.g. above about 100° C.) in water and base.

Lubricants which comprise fluorocarbon substances or other fluorine-containing compounds are desirable for their superior tribological properties characteristic of fluorine-containing substances. These fluorinated substances, such as the Fomblin TM fluids available from Montedison, or the Krytox TM fluids and waxes available from E.I. DuPont de Nemours Co., are soluble only in Freon or Halon solvents, e.g. chlorofluorocarbon (CFC) solvents such as Freon TM 112 or Freon TM 114 commercially available from E.I. DuPont de Nemours Co. Such solvents, however, are subject to regulations based on the Montreal Protocol on Substances that Deplete the Ozone Layer (1987). The term "tribological" used to denote substances which modify surface friction and wear propennies.

It would be desirable to have a lubricant soluble in non-CFC solvents such as tetrahydrofuran and acetone, yet to maintain the tribological characteristics of known fluorine-containing solvents. The lubricant is also desirably stable in the presence of water, acid and base.

SUMMARY OF THE INVENTION

The present invention is directed to lubricating polymers, preferably fluids, advantageously polymeric and oligomeric, preferably dimers and/or polymers thereof, said lubricants being poly(perfluorocyclobutane aryl ether) compounds, and their use as lubricants.

The invention is further directed to lubricants comprising at least one compound having a perfluorocyclobutane group, one or more of the above-described compounds.

The compounds and compositions of the present invention are useful as extended temperature lubricants and as lubricants for magnetic media and in engines, particularly high-temperature engines, particularly when exposed to temperatures in excess of about 200° C.

The compounds are advantageously solvent compatible, magnetic recording media lubricants. Additionally the lubricants are stable in acids, bases and water and at high temperatures, such as from about 35° C. to about 200° C.

The invention includes high density, state of the art recording media, such as high density rigid disks, ultra high density floppy disks, digital audio tape, 8 mm video tape and super VHS tape including a lubricant which may be used as an internal or topical lubricant system to minimize wear and improve overall performance, and to protect the media from damage from the reading and/or writing head of a disk assembly.

The magnetic recording media containing a lubricating amount of lubricants of the invention comprises a substrate; a magnetic recording media thereon which include (a) magnetic particles for recording information; a binder for suspending the magnetic particle and a poly(perfluorocyclobutane aryl ether); or (b) a metallic film for recording information and a poly(perfluorocyclobutane aryl ether) fluid. The media described in (a) is referred to herein as particulate media and in (b), as thin film magnetic media. The lubricants are referred to as internal and topical, respectively.

The lubricant is utilized as a topical lubricant for thin film or non-porous hard and flexible magnetic media advantageously by coating a metallic alloy lamina onto a base polymeric film (e.g. polyester) and applying the lubricant, preferably as a solution in a volatile solvent, to the surface. After solvent evaporation, a thin lubricant layer is left absorbed or bonded to the recording lamina surface.

Alternatively, the lubricant is utilized in an internally lubricated system by preparing a lubricant containing lamina for application to a recording substrate. The lamina is advantageously prepared by forming a dispersion of solvent, a pigment containing magnetic particles and a binder system (e.g. urethane-vinyl). The lamina is then applied to a base film (e.g. polyester, particularly polyethylene terephthalate polyester).

This invention additionally includes a method of preparing magnetic media by forming a dispersion comprising a binder, a magnetic particle containing pigment, a lubricating amount of a poly(perfluorocyclobutane aryl ether), and a surfactant; orienting the magnetic particles by application of a magnetic field; evaporating the solvent; and curing the polymer binder.

Also, the invention includes a method of lubricating magnetic recording media using a composition comprising at least one poly(perfluorocyclobutane aryl ether) compound.

The invention also includes a process of preparing a lubricating poly(perfluorocyclobutane aryl ether) composition comprising heating, to a temperature of at least about 50° C. and sufficient to form perfluorocyclobutane rings from perfluorovinyl groups, a mixture of at least one of the following:
  (a) monomers having two dimerizable perfluorovinyl groups and end-capping agents having one dimerizable perfluorovinyl group;
  (b) monomers having three or more dimerizable perfluorovinyl groups and end-capping agents having one dimerizable perfluorovinyl group; or
  (c) monomers having two or more dimerizable perfluorovinyl groups and endcapping agents having one dimerizable perfluorovinyl group.

Recording media containing the lubricant of the present invention advantageously have improved physical and magnetic durabilities from more effective lubrication. Advantageously, there is also processability in manufacturing because the lubricants are solvent compatible in organic solvents such as toluene, acetone, ethanol and tetrahydrofuran. This makes the product more practical to produce. Furthermore, the lubricants are advantageously stable in acids, bases and water.

DETAILED DESCRIPTION OF THE INVENTION

The poly(perfluorocyclobutane aryl ethers (hereinafter lubricant polymers) of the invention are formed by thermal reaction (dimerization) of monomers having at least one dimerizable perfluorovinyl group such that at least one perfluorocyclobutane group is formed. Whereas polyaddition of perfluorovinyl groups to form perfluoroaliphatic polymers (like polytetrafluoroethylene), not generally having perfluorocyclobutane groups, takes place in the presence of free radicals or free radical generating catalysts, dimerization to form perfluorocyclobutane groups takes place thermally. When a perfluorovinyl group is dimerizable, dimerization is preferably favored over other thermal reactions either kinetically or in equilibrium. Lubricant polymers of the invention are preferably formed by the reaction of monomers having two or more dimerizable perfluorovinyl groups with other monomers having one dimerizable perfluorovinyl group in order to prepare oligomeric compounds which are end-capped with unsubstituted or optionally inertly or reactively substituted aryl ether groups where inert substitution is any substitution which does not interfere undesirably with the formation of the polymers and their lubricating ability and reactive substitution may interfere somewhat but has an advantage of providing better adhesion of the lubricant to a surface being lubricated. Examples of reactive substituents include hydroxyl, amine, and carboxylic acid groups. A dimerizable perfluorovinyl group is a perfluorovinyl group which reacts with another such group to form a perfluorocyclobutane ring. Thus, resulting dimers have one and polymers have at least two perfluorocyclobutane groups, in particular, sufficient perfluorocyclobutane groups to achieve physical and tribological properties desired for specific uses of the polymers.

The term "polymer" is used herein to refer to any compound having at least two perfluorocyclobutane groups formed from perfluorovinyl groups, and includes oligomers which have from about 2 to about 1000 repeating units and preferably have a molecular weight of from about 300 to about 600,000. Fluids used in the practice of the invention are advantageously of weight average molecular weights less than about 75,000, preferably from about 348 to about 10,000, more preferably from about 348 to about 3000; solid thermoplastic polymers useful as lubricants in the practice of the invention advantageously have weight average molecular weights equal to or greater than about 75,000, preferably from about 60,000 to about 600,000, more preferably from about 60,000 to about 200.000; cured thermoset polymers of the invention are useful when sufficiently cured to form solids, advantageously as a layer on a surface to be lubricated, the molecular weight of which layer is not measurable as weight average molecular weight and is referred to as infinite molecular weight because of crosslinking. Within this scope and depending on the molecular structure connecting the perfluorocyclobutyl groups, the number of perfluorocyclobutane groups can vary from as few as two up to hundreds. Additionally encompased in the invention are lubricant compositions comprising dimers of perfluorovinyl compounds, said dimers having a perfluorocyclobutane group.

The relative proportion by weight of the perfluorocyclobutane groups to the other molecular components of the resulting products can vary over a wide range of from about 3 to 1 to about 0.01 to 1, preferably from about 3 to 1 to about 0.05 to 1 and most preferably from about 1 to 1 to about 0.1 to 1. High proportions of perfluorocyclobutane groups are desirable for instance, when fluorocarbon character such as low dielectric constant is beneficial in the products. Exemplary of such products are low dielectric fluids and lubricants.

The poly(perfluorocyclobutane aryl ethers) (lubricant polymers) of the present invention are preferably mixtures of polymeric and dimeric compounds although lower and higher oligomers such as trimers and tetramers are optionally used. The polymeric lubricants preferably have weight average molecular weights ($M_W$) corresponding to greater than about 30 repeating units, more preferably greater than about 35 repeating units. In the case of fluid lubricants, the number of units is preferably sufficiently small that the lubricants are pourable liquids at room temperature and yet maintain a low volatility, usually of a $M_w$ corresponding to less than about 200 repeating units, preferably less than about 100, more preferably less than about 50 repeating units.

Polymeric and/or oligomeric perfluorocyclobutane ring containing lubricants include linear molecular structures prepared from a mixture of monomers having two dimerizable perfluorovinyl groups and end-capping agents having one dimerizable perfluorovinyl group; and branched molecular structures prepared from a mixture of monomers having three or more dimerizable perfluorovinyl groups and end-capping agents having one dimerizable perfluorovinyl group, or mixtures of linear and branched structures prepared from a mixture of monomers having two or more dimerizable perfluorovinyl groups and end-capping agents having one dimerizable perfluorovinyl group. To form the linear polymers, molar ratios of monomers having two dimerizable perfluorovinyl groups to end-capping agents are advantageously from about 1:10 to about 10:1, preferably from about 1:5 to about 5:1, more preferably from about 1:4 to about 4:1. The branched molecular structures are advantageously prepared from a mixture wherein the ratio of monomers having three or more dimerizable perfluorovinyl groups to endcapping agents are preferably from about 1:20 to about 1:1.5, more preferably from about 1: 15 to about 1:2, most preferably from about 1:3 to about 1: 10. The mixtures of linear and branched structures are prepared from a mixture having ratios of monomers having two dimerizable perfluorovinyl groups to monomers having more than two dimerizable perfluorovinyl groups to end-capping agents advantageously of from about 1:0.1:1.5 to about 1:200:2000, preferably from about 1:0.5:2 to about 1:100:500, more preferably from about 1: 1:5 to about 1:10:400. Lubricants which are prepared from the ratios stated above do not necessarily correspond to these ratios of monomer units in the final lubricant composition, because volatile components comprising primarily the dimer of the end capping agent may optionally be removed from the lubricant by distillation or vacuum evaporation.

Linear molecular structures are advantageously easy to prepare in high yields, while the branched molecular structures often perform better as lubricants under higher temperature or higher stress conditions when compared to lubricants which have substantially linear molecular structures. Monomers useful in the practice of the invention are suitably prepared by any method which links molecular structures having perfluorovinyl groups to other molecular structures or which forms perfluorovinyl groups. Useful syntheses are given, for instance in U.S. Pat. No. 5,037,917 which is incorporated herein by reference in its entirety.

Although any monomer having at least one dimerizable perfluorovinyl group is suitably used in the practice of the invention, perfluorovinyl aryl ethers are preferred.

Preferably, to avoid rearrangement and facilitate polymer formation the monomers have structures such that resulting polymers have hydrocarbyl groups (preferably aromatic rings), perfluorocyclobutane rings and at least one noncarbon atom such as oxygen, silicon, boron, phosphorus, nitrogen, selenium, tellurium and/or sulfur atom (each optionally substituted) in the backbones, preferably between the aromatic (aryl) group and the perfluorovinyl group.

The monomers preferably have a structure represented by Formula I:

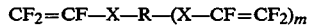

$CF_2=CF-X-R-(X-CF=CF_2)_m$ wherein R represents an, optionally inertly substituted aromatic group; each X is independently any group which links R and a perfluorovinyl group (hereinafter linking structures) preferably an oxygen or sulfur atom, said structures being inert; m+1 is the number of $-X-CF=CF_2$ units. Advantageously, m is an integer of from 0 to about 3, preferably from 0 to about 2. By "inert" it is meant that the structures or substituents do not react undesirably with perfluorovinyl groups or interfere undesirably with polymerization (perfluorocyclobutane formation) of the monomers.

R is suitably any inert molecular structure, preferably a molecular structure which facilitates formation of perfluorocyclobutane rings and/or imparts desirable physical properties to polymers or oligomers prepared from the monomers. Preferably, at least one carbon atom of R is in the molecular chain between X's and is part of an aromatic nucleus. Aromatic groups are desirable because of improved physical properties of the polymers and ease of manufacture of the monomers. For both ease of manufacture of the monomer and monomer stability, when R is aromatic, each X is preferably independently sulfur or oxygen. The aromatic group can be any molecular structure having aromatic character, advantageously having at least one six membered aromatic ring, suitably having any number of such six-membered rings fused together or connected by bonds or linking structures. R preferably has from about 1 to about 50 such rings, more preferably from about 1 to about 10 rings, more preferably containing from about 6 to about 25 carbon atoms, most preferably R has at least 2 to about 4 aromatic rings to impart properties such as hardness and/or stiffness to a polymer. The aromatic fragment is suitably unsubstituted or inertly substituted. Inert substituents on an aromatic R include, for instance, the inert substituents listed for R generally. Optionally R contains groups or has substituents which are inert, that is which do not undesirably interfere with the formation of perfluorocyclobutane rings from perfluorovinyl groups. Inert substituents include ether, carbonyl, ester, tertiary amide, carbonate, sulfide, sulfoxide, sulfone, nitrile, alkyl phosphonate, tertiary amine, alkyl phosphate, alkyl silyl, chlorine, bromine, fluorine, alkyl, arylalkyl, alkylaryl, cycloalkyl, fluoroalky, perfluoroalkyl, aromatic, heterocyclic, alkoxyl, aryloxy groups and the like, which inert substituents are suitably in any position, for instance, in a polymer backbone between X's and/or appended to such a backbone. Molecular structures R and substituents on R are advantageously fluorinated in order to increase the fluorine content of the lubricant and thereby improve it's tribological properties. This may be achieved by substituting the R group with such substituents as fluorine, trifluoromethyl ($CF_3$), perfluoroalkyl or perfluoroalkoxy, or pentafluorosulfanyl. Carbon-containing inert substituents on R preferably contain from about 1 to about 50, more preferably from about 1 to about 12 carbon atoms because of the stability and ease of working with monomers of lower molecular weight. R, including inert substituents preferably has a molecular weight (MW) of from about 14 to about 20,000, more preferably from about 75 to about 15,000 and most preferably from about 75 to about 5.000. These ranges include monomeric and oligomeric R groups. In the case of monomers which are other than oligomeric, R preferably has from about 1 to about 50, more preferably from about 6 to about 25, carbon atoms because molecular weights above this reduce the contribution to properties made by the fluorine-containing substituents when R is alkyl or aromatic hydrocarbon. As previously discussed, the nature of R as well as the perfluorocyclobutane content of the polymers can vary broadly according to the type of products desired.

Exemplary aromatic molecular fragments include, for instance, perchlorophenylene, phenylene, biphenylene, naphthylene, dichlorophenylene, benzophenone, nitrophenylene, p,p'(2,2-diphenylene propane) [—C$_6$H$_4$—C(CH$_3$)$_2$—C$_6$H$_4$]; p,p'-(2,2-diphenylene-1,1,1,3,3,3 hexafluoropropane), [—C$_6$H$_4$—C(CF$_3$)$_2$—C$_6$H$_4$—], 1,4-bis(hexafluoroisopropyl)benzene[—C(CF$_3$)$_2$—C$_6$H$_4$—C(CF$_3$)$_2$—],1,3-bis(hexafluoroisopropyl)benzene [—C(CF$_3$)$_2$—C$_6$H$_4$—C(CF$_3$)$_2$—], preferably biphenylene; phenylene; 9,9'-diphenylfluorene, oxydiphenylene; thiodiphenylene; 2,2-diphenylene propane; 2,2'-diphenylene, 1,1,1,3,3,3-hexafluoropropane; 1,1-diphenylene-1-phenylethane; naphthalene; and anthracene. Molecular weights of aromatic ring containing polymers are preferably at least about 1,000.

Most preferably, at least one aromatic carbon atom of R is bonded directly to X, most preferably aromatic carbon atoms of R are bonded directly to each X because perfluorovinyl groups bonded to X, said X being bonded to aromatic groups are generally more reactive in forming perfluorocyclobutane rings.

Polymers produced from the preferred monomers preferably have a formula represented by Formula 2:

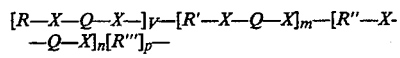

wherein each of R, and R''' are the same or different aromatic groups referred to herein as end capping groups because they are derived from monomers having one dimerizable perfluorovinyl group; R' is a branching group derived from a compound having at least 3 dimerizable perfluorovinyl groups; R'' is an unbranched chain extending group derived from compounds having 2 dimerizable perfluorovinyl groups; Q is a cyclobutane group; X is defined as for Formula 1. Subscripts v, m, n, and p are integers representing the number of groups in the brackets preceeding them such that they correspond to the general formula v+p=a(m)+2 wherein "a" corresponds to the number of dimerizable perfluorovinyl groups on R' minus 2. Thus, when the number of dimerizable perfluorovinyl groups on R' is 3, the formula is v+p=m+2, whereas when the number of dimerizable perfluorovinyl groups on R'=4, the formula is v+p=2m+z, and so on.

Preferred polymers for this purpose are those having a structure represented by Formulas 3 or 4:

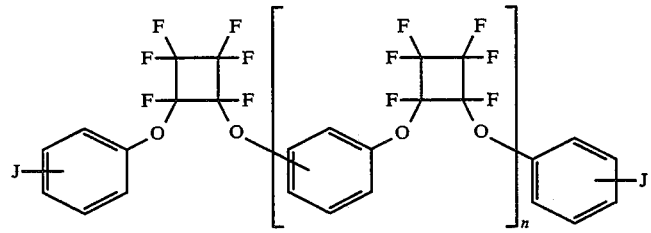

Formula 3 wherein J is H, an inert or reactive substituent. When J is a reactive group or other group capable of substantial dipolar interaction such as hydrogen bonding or strong Vander Waals forces, such groups advantageously serve to adhere the lubricant fluid or polymer more strongly to the media surface. Substituents J are preferably selected from hydrogen, trifluoromethyl, pentafluorosulfanyl, fluorine, perfluoroalkoxy, tetrafluoroethoxy, trifluoromethoxy, methoxy, cyano, carboxylic acid, carboxylate alkyl ester, sulfonate alkyl ester, alkyl or aryl sulfones, amide, alkyl phosphonates, piperanyl, amino and alcohol groups. In each case an alkyl or alkoxy group preferably has from 1 to about 12 carbon atoms, and an aryl group preferably has from about 6 to about 20 carbon atoms.

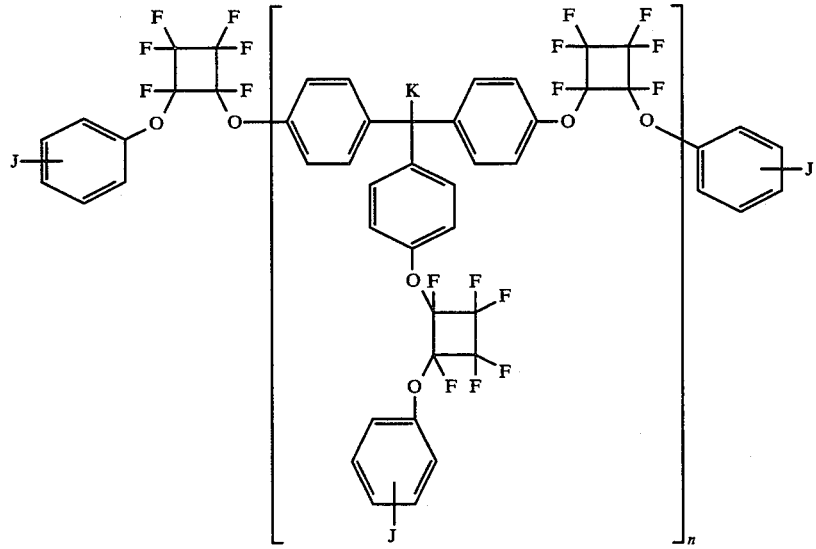

Formula 4 wherein K is an unsubstituted or inertly substituted hydrocarbyl group (aryl, arylalkyl, alkylaryl, linear, branched or cyclic aliphatic), preferably selected from methyl, phenyl, or trifluoromethyl; and J is as described for Formula 3, preferably selected from hydrogen, perfluoroalkoxy, tetrafluoroethoxy, trifluoromethyl, pentafluorosulfanyl, fluorine, trifluoromethoxy, methoxy, cyano, carboxylic acid, carboxylate alkyl ester, sulfonate alkyl ester, alkyl or aryl sulfones, amide, alkyl phosphonates, piperanyl, amino and alcohol groups.

The monomers are heated to a temperature and for a time sufficient to form perfluorocyclobutane rings. Temperatures suitable for forming perfluorocyclobutane rings differ with the structure of the monomer. In general, temperatures above about 40° C. are suitable for formation of perfluorocyclobutane rings, preferably the temperature is above about 50°C., more preferably above about 100°C., because these temperatures result in formation of the rings at successively faster rates. Temperatures above about 450° C. are preferably avoided because perfluorocyclobutane groups are generally thermally unstable above such temperatures. More preferably a temperature of from about 105° C. to about 350° C., most preferably from about 105° C. to about 250° C., is used to produce the perfluorocyclobutane rings at a convenient rate. Within that range, a temperature of from about 130° to about 230° is generally most preferred for cyclization of perfluorovinyl aromatic or aliphatic ethers or sulfides, while a temperature of from about 50° C. to 80° C. is needed to form perfluorocyclobutane groups when the perfluorovinyl group is attached directly to an aromatic ring. In the case of perfluoroalkyl perfluorovinyl ether groups, however, temperature of at least about 300° C., preferably at least about 350° C., is generally required.

Preferably, especially when the perfluorovinyl compounds are capable of radical initiated addition polymerization, conditions conducive to free radical polymerization, e.g. presence of oxygen, ozone, peroxygen compounds and other free radical generating compounds are avoided so that the perfluorovinyl groups will dimerize into perfluorocyclobutane groups rather than undergoing addition polymerization. Compounds known in the art for stabilization against free radical polymerization are alternatively used. Similarly, especially when the perfluorovinyl groups are capable of addition polymerization in the presence of anions or cations, compounds which supply such anions or cations are avoided. For instance, fluoride ions (e.g. from carbonyl fluorides or metal fluorides) chloride, hydroxide, phenoxide and the like are preferably avoided. To avoid such compounds as carbonyl fluorides, oxidative conditions such as presence of oxygen, hypochlorite, dichromate, permanganate and the like are preferably avoided because perfluorovinyl groups are known to oxidize to form carbonyl fluorides. Perfluorovinyl ethers, thioethers, sulfones, sulfoxides and the like are relatively stable with regard to addition polymerization and oxidation; and, therefore, such precautions are generally unnecessary when such perfluorovinyl compounds are used.

Monomers or admixtures thereof are suitably neat or, optionally, in admixture with other materials such as in solution, in emulsion, in dispersions or in any other form in which monomer molecules can be contacted with one another to form a polymer. Liquid admixtures are advantageous for maintaining contact between monomer molecules such that higher molecular weight polymers are formed. This is particularly useful when linear thermoplastic polymers are the products. Neat polymerizations or oligomerizations are also generally preferred to form relatively low molecular weight fluid products. Alternatively, in the case of monomers containing three or more dimerizable perfluorovinyl groups, the polymerization or oligomerization may be carried out in the presence of a large excess of the end-capping agent, which compound contains only one dimerizable perfluorovinyl group. This synthetic method creates an excess of the fluid product containing one perfluorocyclobutane ring, which then acts as a solvent for the production of the branched lubricant prepared from the end-capped monomer containing three or more dimerizable perfluorovinyl groups. This method also advantageously maintains a low molecular weight in the branched lubricant fluid. By carrying out the polymerization in an excess of end-capping agent, a polyfunctional monomer is less likely to react with other polyfunctional monomers to create sufficient networking in the molecular structure to form gels or other insoluble products.

Suitable solvents are those which are inert to the conditions encountered in the polymerization reaction and include perfluorotetradecahydrophenanthrene (MULTIFLUOR TM APF 215 commercially available from Air Products Corp.). At atmospheric pressure, preferred solvents are those which attain temperatures of 170°–250° C. such as dichlorobenzene, trichlorobenzene, diphenyl oxide, perfluorotetradecahydrophenanthrene, and mesitylene. Although solvents such as 1,2-dichlorobenzene and 1,2,4-trichlorobenzene give less satisfactory results such as discoloration of the finished polymer, they are suitably used when their disadvantages are tolerable in a final product. When a solvent is used the concentration of monomers in solvent is advantageously from about 0.1 to about 99.9 weight percent preferably, from about 10 to about 90 percent by weight monomer.

Polymerization or dimerization suitably takes place at any pressure. Pressures are generally chosen such that the monomers and any solvents and/or dispersing media remain liquid at the temperatures used for polymerization. When the monomers or other materials evaporate at temperatures used, then it is generally preferable to maintain a pressure at least sufficient to maintain the materials liquid.

While the compounds of the present invention are described as single molecules having specified substituents present in a stated ratio, it will be realized by one skilled in the art that the compounds will exist as statistical mixtures of molecules. Some of these molecules will have the specified ratio of substituents while others will have higher or lower ratios. However, the perfluorocyclobutane ring containing fluids will, within these statistical mixtures, have substituents present at the specified ratios.

The product is then recovered using conventional techniques, such as by evaporation of the polymerization solvent or light components of the polymerization under reduced pressure, including the end-capping compound which contained one dimerizable perfluorovinyl group, as well as the dimer of the end-capping compound which contained one dimerizable perfluorovinyl group.

The compounds of this invention are useful as lubricants over extended temperature ranges. They may be used alone and also may be used in conjunction with various additives to improve their performance. Additionally, they may themselves be used as additives with other base stocks. Advantageously, the polymers are used at temperatures of from about 50° C. to about 350° C., preferably from about 20° C. to about 200° C.

When used as an additive to a base stock, the poly(perfluorocyclobutane aryl ether) of the present invention must be compatible with the base stock. By compatible, it is meant that the poly(perfluorocyclobutane aryl ether) of the present invention is readily dispersible or soluble in the base stock, either with or without the addition of an appropriate surfactant. Examples of known lubricant base stocks useful in the compositions of this invention include organic oils and greases within the skill in the art. When the poly(perfluorocyclobutane aryl ethers) of the present invention are used as additives to conventional, compatible base stocks, it is preferred that the base stocks are poly alpha olefins, polyglycols, polyphenyl ethers and polyol esters. It is more preferred that the base stocks are polyphenyl ethers such as 5P4E (a polyphenyl ether having 5 phenyl rings with 4 ether linkages, such as that commercially available from Monsanto Corp. under the trade designation OS-124). Other preferred base stocks include polyol esters such as pentaerythritol tetra $C_5$–$C_9$ esters (PET), and poly alpha olefins.

The lubricant compositions of this invention comprise from about 0.1 to about 100 weight percent of the poly(perfluorocyclobutane aryl ether) of the invention. That is, the poly(perfluorocyclobutane aryl ether) of this invention may be used as a lubricant base stock [i.e., lubricant composition is up to about 100 weight percent poly(perfluorocyclobutane aryl ether)] or they may be used as additives with other lubricants [i.e., lubricant composition contains at least about 0.1 weight percent poly(perfluorocyclobutane aryl ether)].

When the poly(perfluorocyclobutane aryl ethers) of this invention are used as lubricant additives, it is preferred that they are used in amounts of at least about 0.5 weight percent, more preferably at least about 5 weight percent. It is also preferred that the poly(perfluorocyclobutane aryl ethers) of the present invention, when used as additives, are used in amounts of no greater than about 50 weight percent, preferably no greater than about 20 weight percent.

As discussed above, the poly(perfluorocyclobutane aryl ethers) of the present invention may be used as lubricants themselves, either alone or with the addition of additives or other lubricants known in the art. When used as the lubricant base stock, additives useful in high temperature lubricants may be added. In this context, it is preferred that the poly(perfluorocyclobutane aryl ethers) of this invention comprise at least about 50 weight percent, more preferably at least about 95 weight percent of the composition with one or more additives making up the remainder of the lubricant composition. Additionally, the poly(perfluorocyclobutane aryl ethers) of this invention may be blended with other base stocks to prepare lubricants.

A preferred embodiment of the present invention is a magnetic recording media comprising a substrate having a magnetic recording lamina thereon, the lamina comprising magnetic particles with a binder in the case of particulate media or without a binder in the case of thin film media, for instance nickel-cobalt. The lamina includes a lubricating amount of at least one poly(perfluorocyclobutane aryl ether) which may be used as either an internal or topical lubricant. Effective poly(perfluorocyclobutane aryl ethers) for this purpose are preferably substituted with fluorine, trifluoromethyl, trifluoromethoxy, tetrafluoroethoxy, perfluoroalkyoxy, methoxy, cyano, carboxylic acid, carboxylate alkyl ester, sulfonate alkyl ester, alkyl or aryl sulfones, amide, pentafluorosulfanyl, alkyl phosphonates, piperanyl, amino and alcohol groups. In each case an alkyl or alkoxy group preferably has from 1 to about 12 carbon atoms, and an aryl group preferably has from about 6 to about 20 carbon atoms.

A preferred embodiment of the present invention is a magnetic recording media comprising a substrate having particulate or thin film magnetic recording lamina thereon, the lamina comprising magnetic particles with a binder or consisting of a metallic film (e.g. nickel-cobalt) without a binder, respectively. The lamina includes a lubricating amount of a perfluorocyclobutane aryl ether polymer which may be used as either an internal or topical lubricant. Effective poly(perfluorocyclobutane aryl ethers) for this purpose are advantageously substituted with fluorine, trifluoromethyl, trifluoromethoxy, tetrafluoroethoxy, perfluoroalkoxy, methoxy, cyano, carboxylic acid, carboxylate alkyl ester, sulfonate alkyl ester, alkyl or aryl sulfones, amide, pentafluorosulfanyl, alkyl phosphonates, piperanyl, amino and alcohols. In each case an alkyl or alkoxy group preferably has from 1 to about 12 carbon atoms, and an aryl group preferably has from about 6 to about 20 carbon atoms.

The lubricant polymers described herein are particularly useful as topical lubricants for thin film magnetic recording media. Thin film magnetic recording media generally include a substrate which may be a non-magnetic metal or a plastic such as a polyester (e.g. polyethylene terephthalate). A magnetic film such as a metal or a metal alloy such as cobalt-nickel is applied to the substrate. The thickness of the magnetic layer is on the order of 0.20 micrometers. The lubricant is preferably on the surface of the magnetic layer preferably 10 to about 1000 Angstrons ($10^{-9}$ to $10^{-7}$m), more preferably from about 2.0 nanometers to about 0.20 micrometers ($2 \times 10^{-9}$ to $2 \times 10^{-7}$m).

Similarly, the lubricant polymers are useful in particulate magnetic recording media. Particulate magnetic recording media generally include a substrate which may be a non- magnetic metal or a plastic such as polyester. Magnetic particle containing pigments such as cobalt gamma $Fe_2O_3$, barium ferrite or iron metal and the like, with a binder are applied to the substrate. The amount of pigment can vary from about 17.0 to about 21.0 weight percent based on total formulation weight. The preferred range is from about 17.0 to about 19.0 weight percent. The binder is advantageously a thermosetting resin such as urethane, vinyl or a combination thereof, present in an amount between about 2.5 and about 6.0 weight percent, based on total formulation weight. The preferred range is between about 3.0 and about 6.0 weight percent.

When used as a topical lubricant for either particulate or thin film media, the poly(perfluorocyclobutyl aryl ether) lubricant is conveniently applied to the surface either neat or in solution with a volatile solvent. Suitable solvents for the lubricant include aromatic hydrocarbons (e.g. toluene), ethers (e.g. diethyl ether, dimethoxyethane, dioxane, tetrahydrofuran, diethoxyethane), halogenated hydrocarbons (e.g. dichloromethane), alcohols (e.g. methanol or ethanol), ketones, (e.g. acetone), esters (e.g. ethyl acetate), alicyclic hydrocarbons (e.g. cyclohexane), dimethylformamide, dimethylsulfoxide, and silicone fluids.

Alternatively, when used as an internal lubricant in particulate magnetic media, the poly(perfluorocyclobutane aryl ether) lubricant is included in the composition of the mixture applied to the substrate to form the recording lamina. This mixture includes binder, pigment containing magnetic particles and a volatile solvent together with the lubricant polymer. Suitable solvents for the lubricant include those listed for topical uses.

Magnetic media containing polymer lubricants of the invention are advantageously prepared in the following way: a dispersion comprising a urethane-vinyl binder and a magnetic particle containing pigment is prepared, e.g. in tetrahydrofuran solvent. Preferred pigments include iron metal, barium ferrite and cobalt gamma $Fe_2O_3$. Pigment to binder ratios are preferably between about 3:1 and about 8:1. Pigment is preferably present in an amount from about 2.5 to about 6.0 weight percent based on total formulation weight. Lubricant is added to the dispersion in an amount preferably between 0 and about 5 weight percent, more preferably from about 0.1 to about 2 weight percent of total formulation weight. A surfactant is added to the composition in an amount preferably between about 0.50 and about 1.0 weight percent of total formulation weight. The magnetic particles are advantageously oriented by application of a magnetic field. Conveniently, the solvent is evaporated and the polymer binder is cured by a thermal process.

Alternatively, the lubricant described herein is used topically in thin film, or non-porous hard and flexible magnetic media.

Coatings of polymeric lubricants are alternatively applied as described in U.S. patent application Ser. No. 07/625,588 filed Dec. 10, 1990 which is incorporated by reference.

Surface treated thin film media containing the lubricant of the present invention compare favorably with media surfaces treated with a hexafluoropropylene epoxide polymer available from E.I. DuPont de Nemours Co. under the trade designation Krytox TM 143 AC and tetrafluoroethylene epoxide polymers commercially available from Ausimont, U.S.A., Inc., under the trade designation Fomblin TM AM 2001. Physical properties including sliding friction and scratch resistance were evaluated to assess surface durability. The results of these comparisons are set forth in Example 8.

The magnetic recording media containing the lubricant polymer of the present invention demonstrate improved surface durability. This is shown in the laboratory sample test results set forth in Examples 8 and 9. The cobalt-nickel thin film magnetic media (tape) coated with poly(perfluorocyclobutane aryl ether) lubricants demonstrate equivalent or improved friction and scratch resistance, when compared to cobalt-nickel thin film magnetic media (tape) coated with Krytox TM 143AC, Fomblin TM AM 2001, or no lubricant. Furthermore, the poly(perfluorocyclobutane aryl ether) lubricants do not require the use of Freon TM or other halogenated solvents in the coating process, whereas Freon TM or other halogenated solvents are needed in the coating process with such lubricants as Krytox TM 143AC and Fomblin TM AM 2001.

Magnetic media containing poly(perfluorocyclobutane aryl ether) lubricants are advantageous in comparison to other commercially available products in that the lubricants of the invention provide optimal physical and magnetic performance such as low static and dynamic coefficients of friction and high coercivitey of underlying or surrounding magnetic media and are economical to produce. A dynamic coefficient of friction obtained is preferably less than about 2, more preferably less than about 0.5, even more preferably less than about 0.25, most preferably less than about 0.16. A static coefficient of friction less than about 0.25.

Furthermore, the poly(perfluorocyclobutane aryl ether)polymers exhibit advantageous enhanced lubricant stability in bases and water.

The following examples are provided for illustrative purposes only and should not be construed as limiting the invention in any way. Unless stated otherwise, all parts, ratios and percentages are by weight. Examples (Ex) of the invention are designated numerically while comparative samples (C.S.) are not examples of the invention and are designated alphabetically.

EXAMPLE 1: PREPARATION OF A FLUID POLYMER OF 1,3-BIS(TRIFLUOROVINYLOXY)BENZENE AND 3-TRIFLUOROVINYLOXY-1',1',1'-TRIFLUOROTOLUENE

To synthesize m-trifluorovinyloxy-1', 1', 1'-trifluorotoluene, DMSO ( 1000 ml), toluene (250 ml), and 3-trifluoromethylphenol (200g, 1.23 mole) are placed in a 2 liter 5-necked flask equipped with a mechanical stirrer, a Dean-Stark trap and a thermocouple attached to a temperature controller. The stirred solution is purged of oxygen by placing a dip tube below the surface of the solution and allowing nitrogen to be blown into the solution for 15 minutes. Potassium hydroxide (45 percent solution, 153.3g, 1.23 mole) is added to the flask all at once, and a line to supply nitrogen is attached to a reflux condenser which is placed on top of the Dean-Stark trap. The mixture is then heated to 85° C. and water is removed azeotropically under a mild vacuum of 100 mm Hg (13.33 kPa) absolute pressure. When water ceases to collect in the Dean-Stark trap, the temperature of the reaction is increased to 125° C. at 100 mm Hg (13.33 kPa) absolute pressure and 100 ml of toluene is removed by distillation, leaving a reaction mixture in the flask.

The reaction mixture is cooled to room temperature, and 1,2-dibromotetrafluoroethane (132.0g, 0.51 mole) is added slowly using a dropping addition funnel. The mixture is heated to 65° C. overnight, then allowed to cool to room temperature. A liquid suspension of potassium bromide (KBr) a by-product of the reaction of 1,2-dibromotetrafluoroethane and potassium 3-trifluoromethyl phenoxide and DMSO (dimethylsulfoxide) is added to a 1.5 times volumetric excess of water in a separatory funnel and shaken vigorously. The product forms a separate, lower layer at the bottom of the funnel and is removed. This crude product (lower layer) is washed again with an equal volume of water. A small amount of toluene is removed from the crude product by evaporation on a rotary evaporator at 30° C. and 20 mm Hg (2.62 kPa) absolute pressure, and the product is thereafter distilled from the crude reaction mixture at 85° C. and 15 mm Hg (2.0 kPa) absolute pressure to provide the product, m-(2-bromotetrafluoroethoxy)-1', 1', 1'-trifluorotoluene (248 g, 0.73 mole, 59 percent yield) as a water white oil. This product gives the following mass spectral data: m/e: 342 (20.1 percent); 340 (19.8 percent); 323 (7.9 percent); 321 (7.2 percent); 211 (25.6 percent); 145 ( 100.0 percent).

The product of the above reaction (248 g, 0.73 mole) is combined with granular zinc (59.0 g, 0.90 mole) in dry acetonitrile (600 ml) and stirred at 83° C. for 4 hours to form a reaction mixture. The mixture is cooled to room temperature and filtered on a 15 micrometer sintered glass filter funnel to remove the zinc salts from the acetonitrile solution of the product. The acetonitrile is distilled out of the crude reaction mixture under reduced pressure (28° C., 150 mm Hg (20 kPa) absolute pressure) after which the product is recovered by distillation at 80° C. and 100 mm Hg (13.33 kPa) absolute pressure to give 158 g (889.7 percent yield) of the product, m-trifluorovinyloxy-1',1',1'-trifluorotoluene, which is 97.8 percent pure by GC (gas chromatographic) analysis, with the remainder of the product being the by-product m-( 1,1,2,2,-tetrafluoroethoxy)- 1',1',1'-trifluorotoluene.

The product gives the following mass spectral data: m/e: 242 (52.3 percent); 223 (12.3 percent); 195 (14.2 percent); 145 (100 percent); 125 (18.3 percent); 95 (30.6 percent).

A mixture is prepared from 1.25 ml of 1,3-bis(trifluorovinyloxy)benzene (as prepared in U.S. Pat. No. 5,023,380) and 8.75 ml of 3-trifluorovinyloxy-1',1',1'-trifluorotoluene to make a total of 10 ml. This mixture is placed in a 50 ml round bottom flask fitted with a nitrogen padded reflux condenser and is refluxed under nitrogen for 20 hours.

The resulting product is analyzed by GC/MS (gas chromatographic mass spectroscopy) and found to be a mixture of hexafluorocyclobutane products whose major components are 1,2-bis(3'-trifluoromethylphenoxy) hexafluorocyclobutane and 1,3-bis(2'-[3"-trifluoromethylphenoxy] hexafluorocyclobutyl)phenyl ether (having two perfluorocyclobutane rings), with a trace amount of 1,2-bis(3'-[2"-{3"-trifluoromethylphenoxy}hexafluorocyclobutyloxy]phenyl)hexafluorocyclobutyloxy]phenyl)hexafluorocyclobutyl ether (having three perfluorocyclobutane rings). By vacuum distillation two fractions are collected.

The first fraction contains primarily mono-perfluorocyclobutane material consisting of two isomers (cis and trans 1,2-substituted hexafluorocyclobutane) with similar mass spectra (given for one isomer only): m/e: 484 (20.2 percent); 465 (12.9 percent); 273 (29.2 percent); 242 (30.1 percent); 207 (11.2 percent); 195 ( 13.0 percent); 145 ( 100.0 percent);

The second fraction contains predominantly di-perfluorocyclobutane material, consisting mainly of three isomers (cis-cis, cis-trans, and trans-trans) of 1,2-substituted hexafluorocyclobutanes, and small amounts of four isomers of a product containing one 1,2-substituted hexafluorocyclobutane ring and one 1,3-substituted hexafluorocyclobutane ring (cis- 1,2 cis- 1,3; cis- 1,2 trans- 1,3; trans-1,2 cis-1,3; and trans-1,2 trans-1,3). All seven products give roughly the same peaks in their mass spectra in differing intensities. The following mass spectral data is for the first product isomer to elute from the gas chromatography (GC) column, and corresponds to one of the three main isomers of two perfluorocyclobutane rings: m/e: 754 (36.4 percent); 593 (12.5 percent); 492 (14.1 percent); 415 (21.9 percent); 273 (27.7 percent); 242 (39.1 percent); 195 (21.5 percent); 173 (23.4 percent); 145 (100.0 percent); 126 (28.5 percent); 95 (23.1 percent); 92 (34.7 percent); 76 (57.6 percent); 64 (27.3 percent).

The second fraction also contains a small amount of material containing three perfluorocyclobutane rings, consisting of six isomers (cis-cis-cis, cis-cistrans, cis-trans-cis, cis-trans-trans, trans-cis-trans, and trans-trans-trans) of 1,2-substituted hexafluorocyclobutanes. Because of the small amount of this product present in the mixture, the corresponding products containing one or more 1,3-substituted hexafluorocyclobutane rings are not detected. The mass spectra of the six isomers showed roughly the same peaks in slightly differing intensities. The following mass spectral data is from the first product isomer of triperfluorocyclobutane material to elute from the GC column: m/e: 1024 (21.6 percent); 593 (16.3 percent); 492 (35.5 percent); 415 (17.6 percent); 281 (16.2 percent); 273 (16.4 percent); 242 (26.0 percent); 208 (15.9 percent); 207 (71.9 percent); 145 (100.0 percent); 92 (19.7 percent); 76 (26.8 percent).

In all cases, the primary products of cyclization are 1,2-substituted hexafluorocyclobutanes, with small amounts (1–2 percent) of 1,3-substituted hexafluorocyclobutanes observable by GC/MS, (except for the triperfluorocyclobutane material, of which only trace amounts are seen) the two being distinguished by a small peak at m/e=100, corresponding to a fragment of $CF_2=CF_2$ present in the mass spectra of the 1,2-substituted hexafluorocyclobutanes which is absent in the 1,3-substituted products. Absolute configurations of the different isomers are not assigned.

This example shows that a compound containing one trifluorovinyl group can be combined with a compound containing two trifluorovinyl groups, the mixture then being heated to cause cyclization of the trifluorovinyl groups to provide a fluid containing perfluorocyclobutane groups. Such fluids are of the type useful as low dielectric hydraulic fluids or lubricants.

EXAMPLE 2: PREPARATION OF A FLUID POLYMER OF 1,3-BIS(TRIFLUOROVINYLOXY)BENZENE (1',1',2',2'-TETRAFLUOROETHOXY)TRIFLUOROVINYLOXYBENZENE AND 1.3-BIS(1',1',2',2'-TETRAFLUOROETHOXY)BENZENE

A mixture (25 ml) consisting of 1,3-bis(trifluorovinyloxy)benzene (as prepared in U.S. Pat. No. 5,023,380) (26 percent), 3-(1', 1',2',2', tetrafluoroethoxy)trifluorovinyloxybenzene (54 percent), 1,3-bis(1', 1',2', 2'-tetrafluoroethoxy)benzene (15 percent),and tetraglyme (5 percent) is placed in a 100 ml round bottom flask and heated at reflux under nitrogen for 5 hours. The resulting viscous oil is checked by GC and is found to contain unreacted 1,3bis(1', 1',2', 2'-tetrafluoroethoxy)benzene and tetraglyme, as well as mixtures of isomers of heavy components. After removal of the light, unreacted components, two fractions are cleanly separated by fractional distillation and each is analyzed by GC/MS.

The first fraction is found to contain primarily 1,2-bis(3'-[1"', 1"',2"',2"'-tetrafluoroethoxy]phenoxy)hexafluorocyclobutane as two isomers (cis and trans substituted hexafluorocyclobutane) followed by small amounts (1–2 percent each) of two 1,3-substituted hexafluorocyclobutane products (cis and trans ), all having roughly similar mass spectra. The following is the mass spectral data for the first isomer to elute from the chromatography column, and corresponds to one of the 1,2-substituted isomers: m/e: 580 (25.8 percent); 371 (11.3 percent); 321 (12.5 percent); 290 (23.4 percent); 270 (36.4 percent); 243 (69.9 percent); 193 (100.0 percent); 95 (96.4 percent); 92 (55.9 percent); 76 (26.7 percent); 64 (29.9 percent); 51 (21.9 percent).

The second fraction contains 1,3-bis(2'-[3''-{1''',1''',2''',2'''-tetrafluoroethoxy}phenoxy]hexafluorocyclobutyl)phenyl ether, primarily as three isomers of 1,2-substituted hexafluorocyclobutanes with a small amount of four isomers of the product with one 1,2-substituted and one 1,3-substituted hexafluorocyclobutane ring. The seven isomers all give roughly the same peaks in their mass spectra in differing intensities. The following mass spectral data is for the first isomer to elute from the GC column, and corresponds to one of the three main isomers of the product: m/e: 850 (24.7 percent); 540 (24.2 percent); 371 (41.5 percent); 321 (12.9 percent); 301 (16.4 percent); 290 (33.9 percent); 270 (74.4 percent); 243 (63.9 percent); 207 (24.1 percent); 193 (86.7 percent); 173 (14.8 percent); 95 (100.0 percent); 92 (63.2 percent), 76 (71.8 percent)64 (32.6 percent); 51 ( 15.5 percent).

This example shows that a compound containing one trifluorovinyl group may be combined with a compound containing two trifluorovinyl groups in a solvent, the resulting mixture being heated to cause cyclization of the trifluorovinyl groups. Such fluids are of the type useful as low dielectric hydraulic fluids or lubricants.

EXAMPLE 3: PREPARATION OF FLUIDS OF 1,1,1-TRIS(4-TRIFLUOROETHENYLOXYPHENYL-ETHANE AND 3-TRIFLUOROETHENYLOXY-1',1'-1'-TRIFLUOROTOLUENE

Samples of 1, 1, 1-tris(4-trifluoroethenyloxyphenyl)ethane (as prepared in U.S. Pat. No. 5,023,380) (60.3g, 0.110 mole) and 3-trifluoroethenyloxy-1'-1'-1'-trifluorotoluene (as prepared in Example 1) (213.9 g, 0.884 mole) are combined in a 250 ml round bottomed flask containing a magnetic stirring bar. A thermocouple is inserted through one neck of the flask into the solution to monitor the temperature. The thermocouple is attached to a temperature controller which controls the power output to a heating mantle on the flask through a Variac rheostat power source. A gas dispersion tube is inserted into the flask below the liquid level, and the liquid is deoxygenated by bubbling nitrogen into the flask with stirring for 15 minutes. The solution is stirred and heated according to the following schedule: 125° C. for 3 hours; 130° C. for 1 hour; 137° C. for 1 hour; 140° C. for 15 hours; 145° C. for 1.5 hours; 150° C. for 3 hours; 160° for 5 hours; 175° C. for 14 hours; 180° C. for 3 hours. The solution is cooled to room temperature, transferred to a 250 ml single necked round bottom flask, and evaporated on a rotary evaporator at 2.0 mm Hg (0.266 kPa) and 160° C. to remove the product 1,2-bis(3-trifluoromethylphenoxy) hexafluorocyclobutane as a 1:1 mixture of cis and trans isomers (168 g, 0.347 mole). This compound is designated Lubricant 1 in Examples 6 and 8.

Mass Spectrometric Analysis, m/e (percent): 75 (12.8 percent); 125 (15.3 percent); 145 (100 percent); 146 (21 percent); 195 (17.4 percent); 242 (15.6 percent); 273 (30.8 percent); 323 (11.4 percent); 465 (55.9 percent); 466 (10.9 percent); 484 (29.2 percent).

The residue from the evaporation is analyzed by gel permeation chromatography (GPC, as standardized against polystyrene) and is found to contain a number of low molecular weight fractions. The lowest molecular weight fraction comprises 42.1 area percent of the GPC curve, analyzed at weight average molecular weight

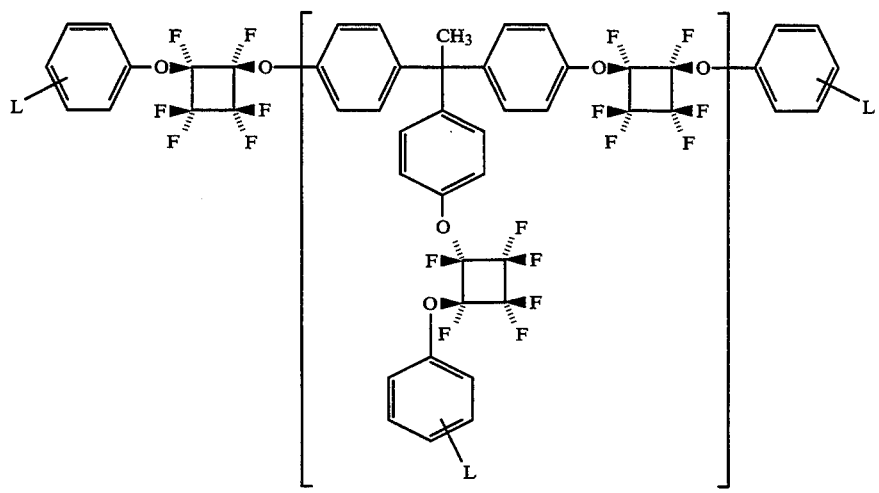

Formula 5 wherein n is from about 0 to about 20, preferably 0 or from 1 to about 20; each L is independently trifluoromethyl, fluorine, trifluoromethoxy, tetrafluoroethoxy, perfluoroalkoxy, methoxy, cyano, carboxylic acid, carboxylate alkyl ester, sulfonate alkyl ester, alkyl or aryl sulfones, amide, pentafluorosulfanyl, alkyl phosphonate, piperaryl, amino or alcohol groups, preferably and in this example trifluoromethyl. Where each alkyl group is preferably from 1 to about 12 carbon atoms and each aryl group is preferably from 6 to about 20 carbon atoms.

1337, corresponding to the compound of Formula 5 with n=1 (calculated molecular weight=1272). The next higher molecular weight fraction comprises 24.8 area percent of the GPC curve, and analyzes at a weight average molecular weight of 2124, corresponding to the compound of Formula 5 with n=2 (calculated molecular weight=2060). The third fraction comprises 14.7 area percent of the GPC curve, and analyzes at a weight average molecular weight of 2921, corresponding to the compound of Formula 5 with n=3 (calculated molecular weight=2848). The remainder of the content of the fluid comprises 18.4 area percent of the GPC curve, and is composed of a mixture of higher molecular weight compounds of Formula 5, with the two components combined in ratios according to the formula $[X]_n[Y]_{n+2}$ where $X=1,1,1$-tris(4-trifluoroethenyloxyphenyl)-ethane and $Y=3$-trifluoroethenyloxy-1'-1'-1'-trifluorotoluene, and n is greater than or equal to 4, and less than or equal to 18. This mixture is designated Lubricant 2 in Examples 7 and 9.

These examples demonstrate the preparation of novel molecular compositions which have a high fluorine content by weight, but which possess alkyl hydrocarbon and aromatic hydrocarbon substituents to increase their compatibility with hydrocarbon organic chemical systems. This increased compatibility with hydrocarbon organic systems allows the application of coatings of these fluids to a substrate surface from a wide variety of hydrocarbon organic solvents, eliminating the need for application from Freon TM solvents which are in disfavor. Such fluid coatings are useful as lubricants to reduce friction and wear.

EXAMPLE 4: FRICTION AND WEAR TEST

The anti-wear and extreme-pressure characteristics of the poly(perfluorocyclobutane aryl ether) lubricant polymers of this invention are measured by pin-on-disk testing. In this example a silicon nitride (SIN) pin with hemispherical tip geometry is slided against a disk made of a film of biphenyl perfluorocyclobutyl ether polymer as prepared in U.S. Pat. No. 5,023,380. Test load range is 2-15 Newtons (0.44 to 3.3 pounds). The sliding speed is 50 cm/sec and each test is run for 120 seconds at 25° C. During each test, the torque as a fraction of the wear cycles is monitored on a real time data acquisition basis for data analysis to yield the coefficient of friction.

The average dynamic coefficient of friction of the biphenyl perfluorocyclobutyl ether polymer is 1.23–0.20. As a comparison the average dynamic coefficient of friction of a 2 mil film of Kapton TM polyimide (commercially available from E.I. Du Pont de Nemours Co.) is 0.90–0.15.

The data in the above example shows that the perfluorocyclobutane ring containing thermoplastic polymer performs favorably when compared to a leading polymeric lubricant film.

EXAMPLE 5: FRICTION AND WEAR TESTS

The procedure of Example 4 is followed with thermoset polymer prepared from 1,1,1,-tris(4-trifluorovinyloxyphenyl) ethane as prepared in U.S. Pat. No. 5,023,380 as the disk composition.

The average dynamic coefficient of friction of the thermoset polymer prepared from 1,1,1-tris(4-trifluorovinyloxyphenyl)ethane is 0.97±0.20. As a comparison the average dynamic coefficient of friction of a 2 mil film of Kapton$^{TM}$ TM polyimide (commercially available from E.I. Du Pont de Nemours Co.) is 0.90±0.15.

The data in the example above demonstrates the perfluorocyclobutane ring containing thermoset polymer performs favorably when compared to a leading polymeric lubricant film.

EXAMPLE 6 AND COMPARATIVE SAMPLE A: ADDITIVE FRICTION AND WEAR TESTS

The anti-wear and extreme pressure characteristics of the compounds and compositions of this invention are measured using the four-ball test using a Falex friction and wear tester according to the manufacturer's directions. In this Example, 1,2-bis(3-trifluoromethylphenyloxy) hexafluorocyclobutane as prepared in Example 3 (with various amounts of a polyphenyl ether, 5P4E (commercially available from Monsanto, Corp. under the trade designation OS-124), the amounts indicated in Table 1 is tested. The four-ball bearing balls used in this test are made of M-50 steel. The test load is 135 Newtons (30 pounds). The test speed is 1200 rpm and each test is run for 1 hour unless noted otherwise. About 60 cubic centimeters ($60 \times 10^{-6} m^3$) of fluid are used for each test. Each test is conducted at 200° C. During each test, the torque is monitored on a real time data acquisition basis for data analysis to yield the coefficient of friction. Optical microscope pictures of the bearing balls are taken at the test completion, and scar diameter is measured from these pictures. The data obtained is shown in Table 1.

TABLE 1

| Test # | Concentration of Lubricant 1 in OS-124 (weight percent) | Scar Diameter (mm) | Coefficient of Friction |
|---|---|---|---|
| C.S.A | 0 | 1.06 | 0.28 |
| Ex. 6 | 10 | 0.88 | 0.16 |

The data shown in Table 1 demonstrates the effectiveness of a compound of the invention as an additive to improve the tribological properties of known lubricants.

EXAMPLE 7 AND COMPARATIVE SAMPLE B: ADDITIVE FRICTION AND WEAR TEST

The procedure of Example 6 is followed with the exception that the poly(perfluorocyclobutane aryl ether) Lubricant 2 as prepared in Example 3 is used in place of 1,2-bis(3-trifluoromethylphenyloxy)hexafluorocyclobutane (Lubricant 1 ) used in Example 6. The results obtained are reported in Table 2.

TABLE 2

| Test # | Concentration of Lubricant 2 in OS-124 (weight percent) | Scar Diameter (mm) | Coefficient of Friction |
|---|---|---|---|
| C.S.B | 0 | 1.06 | 0.28 |
| Ex. 7 | 10 | 0.56 | 0.14 |

The data shown in Table 2 above demonstrates the effectiveness of the compound of this invention as an additive to improve the tribological properties of known lubricants.

EXAMPLES 8 AND 9 AND COMPARATIVE EXAMPLES C, D AND E: EVALUATIONS AS TOPICAL LUBRICANTS ON COBALT-NICKEL MAGNETIC TAPE

Experimental samples of topically-lubricated 8 mm cobalt-nickel magnetic tape are prepared by submerging unlubricated tape into a 0.1 or 1.0 weight percent (as indicated in Table 3) lubricant solution in Freon TM 113 (commercially available from E.I. DuPont de Nemours Co.) or methyl ethyl ketone (MEK). Separate tape samples are prepared with Lubricant 1 (as Example 8) and Lubricant 2 (as Example 9) of the present invention, as well as comparison examples including a hexa-fluoropropylene epoxide polymer commercially available from E.I. DuPont de Nemours Co. under the trade designation Krytox TM 143AC (as C.S. D); tetrafluoroethylene epoxide polymer commercially available from Ausimont U.S.A., Inc. under the trade designation Fomblin TM AM 2001 (as C.S. E); and tape without lubricant (as C.S. C).

Coefficient of friction is measured by the procedure of ASTM D-3028 using a frictionometer commercially available from Custom Scientific Instruments, Inc.

Scratch appearance force and scratch depth are measured by a scratch test performed according to the procedure of ASTM D-2197 except that it is miniaturized by a factor of $10^{-3}$ to measure micrometer rather than millimeter scratches. In this test, a loaded stylus is dragged across a sample surface, and the sample is inspected under 30×magnification to determine whether there is a visible scratch. Stylus load is varied from 0 to 40 mg in 10 mg steps. A commercial profilometer with a stylus radius of 2.5 μm is used for the test and is used to measure the depth of a scratch when one is observed. Depth is measured by retracing the scratch at 90° degrees to the observed scratch with a stylus load 10 mg less than the load used to make the scratch so that the measuring stylus does not increase the scratch depth.

The test results are shown below in Table 3.

TABLE 3

| Example | Solvent | Concentration (weight percent) | Coefficient of Friction | Scratch Appearance Force (mg) | Scratch Depth (nm) (40 mg load) |
|---|---|---|---|---|---|
| C.S.C | Freon 113 | 0 | 0.35 | 30 | 15.0 |
| C.S.D | Freon 113 | 1 | 0.34 | >40 | 0 |
| C.S.E | Freon 113 | 1 | 0.07 | >40 | 0 |
| Ex. 8 | MEK | 1 | 0.08 | 40 | 5.0 |
| Ex. 9 | MEK | 0.1 | 0.22 | 20 | 20.0 |

Test results show test Lubricant 1 and Lubricant 2 which are described in EXAMPLE 3 are effective as topical lubricants for thin film magnetic media and are effectively applied from methyl ethyl ketone rather than a chlorofluorocarbon.

What is claimed is:

1. A lubricant comprising at least one compound having a perfluorocyclobutane group, hydrocarbyl group, and at least one non-carbon atom in the backbone.

2. The lubricant of claim 1 in which the perfluorocyclobutane groups comprise perfluorocyclobutane aryl ether groups.

3. The lubricant of claim 2 which comprises a dimer of a perfluorovinyl aryl ether.

4. The lubricant of claim 2 which comprises a poly(perfluorocyclobutane aryl ether).

5. The lubricant of claim 2 imparting a dynamic coefficient of friction of less than about 0.25.

6. The lubricant of claim 2 comprising a lubricant base stock and at least about 0.1 weight percent of a least one poly(perfluorocyclobutane aryl ether).

7. The lubricant of claim 6 wherein the base stock comprises at least one poly alpha olefin, polyglycol, polyphenyl ether, polyol esters or mixture thereof.

8. The lubricant of claim 7 wherein the base stock comprises at least one polyphenyl ether.

9. The lubricant of claim 7 which comprises at least about 50 weight percent poly(perfluorocyclobutane aryl ether).

10. The lubricant of claim 7 which comprises at least about 95 weight percent poly(perfluorocyclobutane aryl ether).

11. The lubricant of claim 2 which is a liquid comprising polymeric and oligomeric poly(perfluorocyclobutane aryl ether) compounds.

12. The lubricant of claim 11 wherein the poly(perfluorocyclobutane aryl ether), has a weight average molecular weight of equal to or greater than about 75,000, 13. The lubricant of claim 2 wherein the compound having perfluorocyclobutane aryl ether groups is a poly(perfluorocyclobutane aryl ether), and has a weight average molecular weight of from about 60,000 to about 600,000.

14. The lubricant of claim 13 wherein the poly(perfluorocyclobutane aryl ether) is a cured thermoset polymer 15. The lubricant of claim 11 which comprises a mixture of polymeric and dimeric poly(perfluorocyclobutane aryl ether) compounds.

16. The lubricant of claim 15 which is linear.

17. The lubricant of claim 16 which is prepared from a mixture of monomers having two dimerizable perfluorovinyl groups and end-capping agents having one dimerizable perfluorovinyl group.

18. The lubricant of claim 17 wherein the ratio of monomers having two dimerizable perfluorovinyl groups to end-capping agents are from about 1:10 to about 10:1, 19. The lubricant of claim 18 wherein the ratio of monomers having two dimerizable perfluorovinyl groups to end-capping agents are from about 1:5 to about 5:1.

20. The lubricant of claim 15 which has a branched molecular structure

21. The lubricant of claim 20 which is prepared from a mixture of monomers having three or more dimerizable perfluorovinyl groups and endcapping agents having one dimerizable perfluorovinyl group.

22. The lubricant of claim 21 wherein the ratio of monomers having three or more dimerizable perfluorovinyl groups to end-capping agents is from about 1:20 to about 1:1.5, 23. The lubricant of claim 22 wherein the ratio of monomers having three or more dimerizable perfluorovinyl groups to end-capping agents is from about 1:15 to about 1:2.

24. The lubricant of claim 15 which is a mixture of linear and branched structures.

25. The lubricant of claim 24 which is prepared from a mixture of monomers having two or more dimerizable perfluorovinyl groups and end-capping agents having one dimerizable perfluorovinyl group.

26. The lubricant of claim 25 wherein the ratio of monomers having two dimerizable perfluorovinyl groups to monomers having more than two dimerizable perfluorovinyl groups to end-capping agents is from about 1:0.1:1.5 to about 1:200:2000.

27. The lubricant of claim 26 wherein the ratio of monomers having two dimerizable perfluorovinyl groups to monomers having more than two dimerizable perfluorovinyl groups to end-capping agents is from about 1:0.5:2 to about 1:100:500.

28. The lubricant of claim 11 wherein the poly(perfluorocyclobutane aryl ether), has a weight average molecular weight of less than about 75,000.

29. The lubricant of claim 11 wherein the poly(perfluorocyclobutane aryl ether), has a weight average molecular weight of from about 348 to about 10,000.

30. The lubricant of claim 29 wherein the poly(perfluorocyclobutane aryl ether), has a weight average molecular weight of from about 348 to about 3000.

31. The lubricant of claim 2 in which the compound containing perfluorocyclobutane aryl ether groups is a poly(perfluorocyclobutane aryl ether) and has aryl groups substituted with at least one fluorine, trifluoromethyl, tetrafluoroethoxy, trifluoromethoxy, methoxy, cyano, carboxylic acid, carboxylate alkyl ester, sulfonate alkyl ester, alkyl or aryl sulfone, amide, pentafluorosulfanyl, alkyl phosphonate, piperanyl, amine group, alcohol or combination thereof.

32. The lubricant of claim 1 having a formula represented by Formula 2:

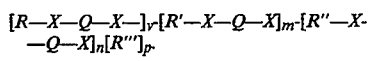

wherein each of R, and R''' are the same or different aromatic groups; R' is a branching group; R" is an unbranched chain extending group derived from compounds having 2 dimerizable perfluorovinyl groups; X is oxygen or sulfur and Q is a perfluorocyclobutane group; subscripts v, m, n, and p are integers representing the number of groups in the brackets preceeding them such that $v+p=am+2$ where $(a+2)$ is the number of dimerizable perfluorovinyl groups on R'.

33. The lubricant of claim 32 wherein R is selected from perchlorophenylene, phenylene, biphenylene, naphthylene, dichlorophenylene, benzophenone, nitrophenylene, p,p'(2,2-diphenylene propane) trifluoroethenyloxyphenyl)-ethane $[—C_6H_4—C(CH_3)_2—C_6H_4]$; p,p'-(2,2-diphenylene-1,1,1,3,3,3 hexafluoropropane), $[—C_6H_4—C(CF_3)_2—C_6H_4—]$, 1,4-bis(hexafluoroisopropyl)benzene$[—C(CF_3)_2—C_6H_4—C(CF_3)_2—]$, 1,3-bis(hexafluoroisopropyl)benzene $[—C(CF_3)_2—C_6H_4—C(CF_3)_2—]$, biphenylene; phenylene; 9,9'-diphenylfluorene, oxydiphenylene; thiodiphenylene; 2,2-diphenylene propane; 2,2'-diphenylene, 1,1,1,3,3,3-hexafluoropropane; 1,1-diphenylene-1-phenylethane; naphthalene, anthracene and mixtures thereof.

34. The lubricant of claim 33 wherein R has at least one fluorine or fluorine-containing substituent in addition to the perfluorocyclobutane rings.

35. The lubricant of claim 1 having a structure represented by at least one of Formulas 3 or 4:

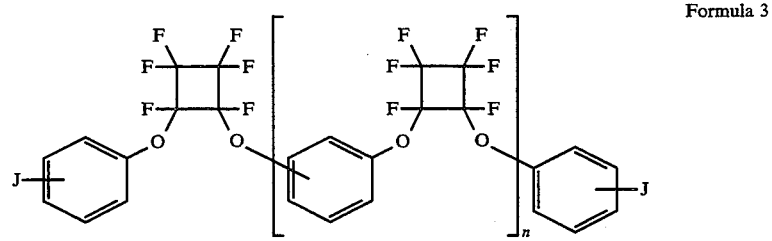

Formula 3 wherein J is H, or an inert or reactive substituent; or

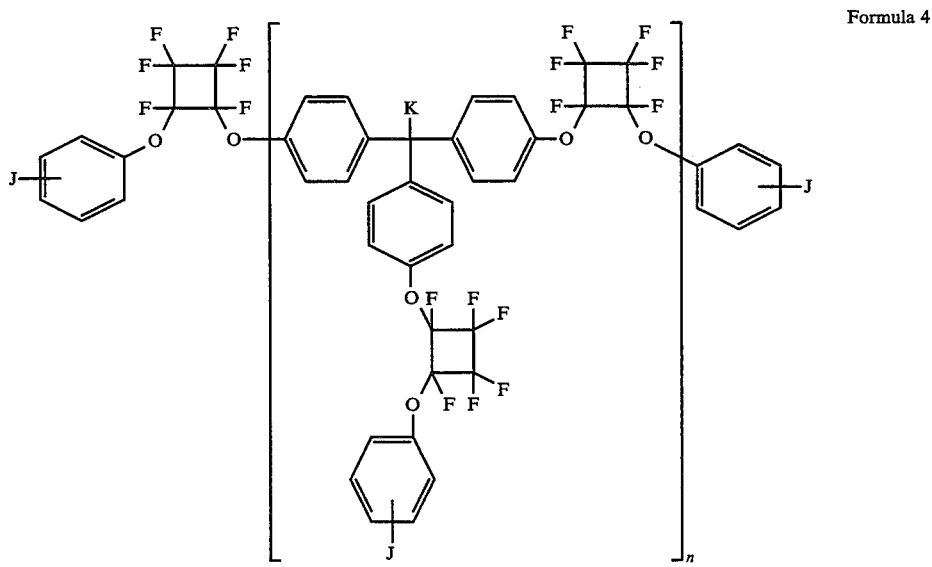

Formula 4 wherein J is as described for Formula 3 and K is an unsubstituted or inertly substituted hydrocarbyl group.

36. The lubricant of claim 1 having a structure represented by Formula 5

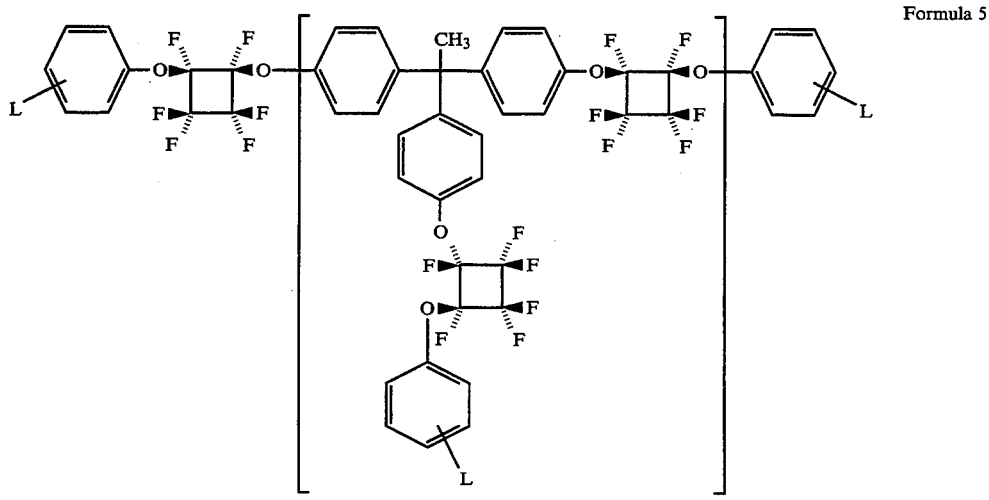

Formula 5 wherein n is an integer of from about 0 to about 20 and L is independently trifluoromethyl, fluorine, trifluoromethoxy, tetrafluoroethoxy, perfluoroalkoxy, methoxy, cyano, carboxylic acid, carboxylate alkyl ester, sulfonate alkyl ester, alkyl or aryl sulfones, amide, pentafluorosulfanyl, alkyl phosphonate, piperaryl, amino or alcohol groups.

37. The lubricant of claim 36 wherein n is an integer of from 1 to about 20.

38. The lubricant of claim 36 wherein n is 0; and L is a trifluoromethyl group.

39. A method of lubricating an engine using a composition comprising at least one poly(perfluorocyclobutane aryl ether) compound.

* * * * *

UNITED STATES PATENT AND TRADEMARK OFFICE
CERTIFICATE OF CORRECTION

PATENT NO. : 5,364,547
DATED : November 15, 1994
INVENTOR(S) : David A. Babb, et. al.

It is certified that error appears in the above-indentified patent and that said Letters Patent is hereby corrected as shown below:

On the title page, in item [56] under "FOREIGN PATENT DOCUMENTS", "030292" should read --0303292--.

In claim 27, column 22, line 56, "1:100:500", delete bold type.

In claim 33, column 24, lines 2 and 3, delete "trifluoroethenyloxyphenyl)ethane".

Signed and Sealed this

Second Day of January, 1996

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,364,547

DATED : November 15, 1994

INVENTOR(S) : David A. Babb and Ted A. Morgan

It is certified that error appears in the above-identified patent and that said Letters Patent is hereby corrected as shown below:

Col. 26, In claim 36, "in Formula 5", the formula should read --

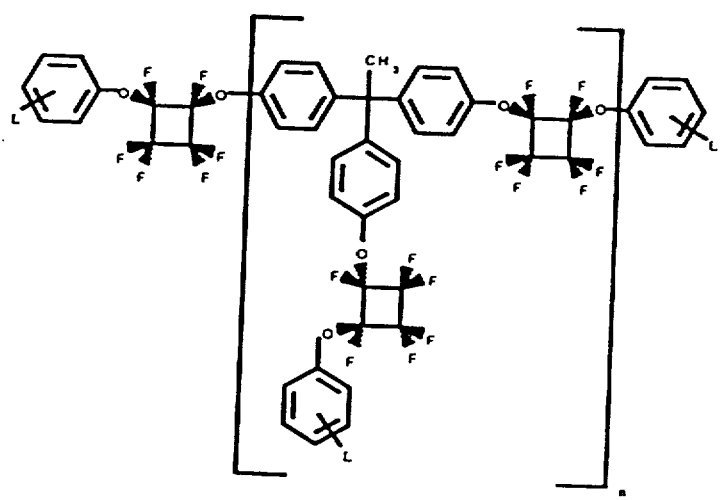

Formula 5

--.